United States Patent [19]

Brismar

[11] Patent Number: 5,432,167
[45] Date of Patent: Jul. 11, 1995

[54] CELL PROLIFERATION MATRIX AND USE THEREOF

[75] Inventor: Kerstin Brismar, Djursholm, Sweden

[73] Assignee: Skandigen AB, Stockholm, Sweden

[21] Appl. No.: 66,165

[22] PCT Filed: Dec. 5, 1991

[86] PCT No.: PCT/SE91/00839

§ 371 Date: Jun. 7, 1993

§ 102(e) Date: Jun. 7, 1993

[87] PCT Pub. No.: WO92/10195

PCT Pub. Date: Jun. 25, 1992

[30] Foreign Application Priority Data

Dec. 6, 1990 [SE] Sweden ............... 9003887

[51] Int. Cl.$^6$ ........................... A61K 31/725
[52] U.S. Cl. ..................... 514/54; 514/925; 514/928; 536/18.7
[58] Field of Search ............... 514/54, 925, 928; 536/18.7

[56] References Cited

U.S. PATENT DOCUMENTS

| | | | |
|---|---|---|---|
| 4,141,973 | 2/1979 | Balazs | 424/180 |
| 4,801,539 | 1/1989 | Akasaka et al. | 435/101 |
| 5,133,755 | 7/1992 | Brekke | 623/16 |
| 5,166,331 | 11/1992 | della Valle et al. | 536/55.1 |
| 5,180,808 | 1/1993 | Ruoslahti | 530/350 |
| 5,196,185 | 3/1993 | Silver et al. | 424/45 |
| 5,234,914 | 8/1993 | Gallina et al. | 514/54 |
| 5,240,710 | 8/1993 | Bar-Shalom et al. | 424/422 |

FOREIGN PATENT DOCUMENTS

| | | |
|---|---|---|
| 138572 | 4/1985 | European Pat. Off. . |
| 266578 | 5/1988 | European Pat. Off. . |
| 312208 | 4/1989 | European Pat. Off. . |

Primary Examiner—Douglas W. Robinson
Assistant Examiner—Kathleen Kahler Fonda
Attorney, Agent, or Firm—Bacon & Thomas

[57] ABSTRACT

A cell proliferation matrix consisting of an aqueous gel of hyaluronic acid or a pharmaceutically acceptable salt thereof which is free from production-related animal DNA and RNA and which is in a dissolved state, is disclosed. Further, the use of hyaluronic acid or a pharmaceutically acceptable salt thereof for the preparation of a cell proliferation matrix according to the invention, for the treatment of at least one of bone fractures, Ulcus Varicosum Cruris, and ulcera caused by Diabetes Mellitus and other diseases (e.g. Decubitus) with impaired arterial blood flow, is described. Also, a method of treating at least one of bone fractures, Ulcus Varicosum Cruris, and ulcera caused by Diabetes Mellitus and other diseases with impaired arterial blood flow is disclosed.

12 Claims, No Drawings

CELL PROLIFERATION MATRIX AND USE THEREOF

The present invention relates to a cell proliferation matrix which consists of an aqueous gel of hyaluronic acid or a pharmaceutically acceptable salt thereof, which is in a dissolved state. It also relates to the use of hyaluronic acid or a pharmaceutically acceptable salt thereof for the preparation of a cell proliferation matrix. Further, it relates to a method of treating at least one of bone fractures, Ulcus Varicosum Cruris, and ulcera caused by Diabetes Mellitus and other diseases with impaired arterial blood flow, wherein the cell proliferation matrix according to the invention is used.

BACKGROUND

Ulcus Varicosum Cruris and ulcera caused by Diabetes Mellitus and other diseases with impaired arterial blood flow, such as Decubitus, are ulcera which are very slow-healing due to defective nutrition of the cells. Such ulcera may not heal in years, and the patients often repeatedly suffer from infections. These are normally treated with antibiotics, but such treatment is not always successful.

Obviously there is a great need of medical aid for the treatment of such slow-healing ulcera.

In EP-312208-A there is disclosed a gel for topical and incisional wound healing comprising a polypeptide growth factor (PGF) having human mitogenic or angiogenic activity and a water soluble or swellable polymer, which i.a. may be hyaluronic acid. The gel is to be applied to gauze to form a wound healing bandage which stimulates cell growth and increases the rate of healing.

DESCRIPTION OF THE INVENTION

It was surprisingly found that an aqueous gel of hyaluronic acid or a pharmaceutically acceptable salt thereof, in a dissolved state, alone functions as a cell proliferation matrix. Since the cell proliferation matrix according to the invention does not only promote epithelial but also endothelial cell growth, it is expected that it will promote osteoblast growth as well. Thus it can be used in the treatment of bone fractures, Ulcus Varicosum Cruris and ulcera caused by Diabetes Mellitus and other diseases with impaired arterial blood flow, such as Decubitus.

Hyaluronic acid is widely distributed in connective tissues in mammals, but only in small quantities, and it is also known to be present in microorganisms. Hitherto hyaluronic acid has mostly been extracted from rooster combs, bovine joints and whale cartilages. However, it forms in the animal tissues complexes with proteins and other mucopolysaccharides, and therefore it is complicated to purify, and thus there is always a risk of contamination by animal DNA and RNA, which may carry DNA and RNA viruses, such as hepatite B virus and HIV virus. Therefore the hyaluronic acid or pharmaceutically acceptable salt thereof which is to be used in the present invention should be free from animal DNA and RNA. Such hyaluronic acid can be produced by microorganisms, and one disclosure of the production of such hyaluronic acid has been published in EP-A-0 266 578. The sodium hyaluronate used in the clinical trials below has been produced by continuous fermentation of Streptococcus equi by FERMENTECH Ltd., Research Avenue South, Riccarton Campus, Edinburgh EH14 4AP, Scotland.

In a preferred embodiment of the cell proliferation matrix according to the invention the aqueous gel is made of 99.9 to 98.0 percent by weight of water or of phosphate buffered saline solution and 0.1 to 2.0 percent by weight of sodium hyaluronate having an average molecular weight of at least 25,000 Da. It is believed that the average molecular weight of sodium hyaluronate is not critical as long as it is at least 25,000 Da and as long as it is in a dissolved state. The average molecular weight of the sodium hyaluronate to be used in the invention is suitably in the range of $1.2 \times 10^6$–$2.5 \times 10^6$ Da. In a preferred embodiment of the invention the cell proliferation matrix consists of an aqueous gel containing 1.0 percent by weight of sodium hyaluronate having an average molecular weight of $1.2 \times 10^6$ Da.

It should be understood that the aqueous gel according to the invention should have a viscosity which allows the hyaluronic acid or a pharmaceutically acceptable salt thereof to be in a dissolved state, so that the molecules can readily function as a cell proliferation matrix. If the concentration of the sodium hyaluronate exceeds 2.0 percent by weight of the aqueous gel, then the viscosity of the gel is probably too high. On the other hand, if the concentration of the sodium hyaluronate is less than 0.1 percent by weight of the aqueous gel, then the gel will probably be too diluted for the gel to stay in place when it is applied to an ulcus or a bone fracture.

Thus, one aspect of the invention is directed to a cell proliferation matrix, which consists of an aqueous gel of hyaluronic acid or a pharmaceutically acceptable salt thereof which is free from production-related animal DNA and RNA and which is in a dissolved state. In one embodiment of this aspect of the invention the aqueous gel is made of 99.9 to 98.0 percent by weight of water or of phosphate buffered saline solution and 0.1 to 2.0 percent by weight of sodium hyaluronate having an average molecular weight of at least 25,000 Da. Suitably the average molecular weight of the sodium hyaluronate is in the range of $1.2 \times 10^6$ to $2.5 \times 10^6$ Da. In a preferred embodiment of the cell proliferation matrix according to the invention the aqueous gel contains 1.0 percent by weight of sodium hyaluronate having an average molecular weight of $1.2 \times 10^6$ Da.

Another aspect of the invention is directed to the use of hyaluronic acid or a pharmaceutically acceptable salt thereof which is free from production-related animal DNA and RNA for the preparation of an aqueous cell proliferation matrix for the treatment of at least one of bone fractures, Ulcus Varicosum Cruris, and ulcera caused by Diabetes Mellitus and other diseases with impaired arterial blood flow, such as Decubitus. The aqueous cell proliferation matrix is preferably in the form of an aqueous gel in which said hyaluronic acid or pharmaceutically acceptable salt thereof is in a dissolved state. The embodiments of this aspect of the invention correspond to the embodiments and preferred embodiments of the cell proliferation matrix according to the invention.

Yet another aspect of the invention is directed to a method of treating at least one of bone fractures, Ulcus Varicosum Cruris, and ulcera caused by Diabetes Mellitus and other diseases with impaired arterial blood flow (e.g. Decubitus), which comprises topically administering to a patient in need of such treatment(s) a therapeutically effective amount of a cell proliferation matrix consisting of an aqueous gel of hyaluronic acid or a pharmaceutically acceptable salt thereof, which is free from production-related animal DNA and RNA and which is in a dissolved state. In an embodiment of this aspect of the invention said cell proliferation matrix consists of an aqueous gel which is made of 99.9 to 98.0 percent by weight of water or a phosphate buffered saline solution and 0.1 to 2.0 percent by weight of sodium hyaluronate having an average molecular weight of at least 25,000 Da.

A therapeutically effective amount of a cell proliferation matrix according to the invention is an amount which promotes healing compared to a blank.

Examples of pharmaceutically acceptable salts of hyaluronic acid are the potassium and the sodium salts.

The aqueous gel according to the invention should be sterile when used. The aqueous gel can be sterilized in an autoclave or by irradiation with gamma rays, or an appropriate amount of sodium hyarulonate may be sterilized in solid form and reconstituted in sterile water before use.

The cell proliferation matrix according to the invention, in the form of an aqueous gel of hyaluronic acid or a pharmaceutically acceptable salt thereof, is applied directly to the ulcus and/or the bone fracture to be treated, whereupon the ulcus is covered with a dry bandage. The application of the cell proliferation matrix according to the invention is suitably effected once or twice a day.

CLINICAL TRIALS

The cell proliferation matrix according to the invention has been used in clinical trials at the Department of Endocrinology, Karolinska Sjukhuset, Stockholm, Sweden. The cell proliferation matrix used in the treatment of the below specified ulcera consisted of a sterile aqueous gel of 1.0 percent by weight of sodium hyaluronate having an average molecular weight of $1.2 \times 10^6$, and of 99.0 percent by weight of phosphate buffered saline solution. Said sodium hyaluronate was from FERMENTECH, Scotland.

CASE 1)

The following outlines the treatment of a male patient, 58 years of age, with insulin treated diabetes type 2 since 10 years, having anamnesis angina pectoris, claudicatio intermittens and hypotalamus infarctus 1986 with recurrent transitory ischemic attacks during the last year. The patient had surgery in July 1989 with righthand-sided nephrectomi and adrenalectomi due to renal cancer engaging capsula and surrounding glandula suprarenalis without sign of spreading to the liver. In conjunction with the nephrectomi the patient developed decubitus on the left heel. The first appearance of the decubitus was as a blister with a diameter of approximately one inch.

An investigation showed general macroangiopathy with weakened peripheral pulses in the left and right leg. As well as further signs of neuropathy with lowered sensibility bilaterally in the feet. The blister developed to necrosis with some infection and was treated with antibiotics during the autumn 1989. The patient was treated until spring 1989 with the effort to normalize the blood sugar, as well as repeated treatment with antibiotics due to recurrence of infections in the heel ulcus which did not heal. Vascular surgery was refused despite stenotic changes due to multiple stenosis from *A. femoralis* down to the feet.

The local treatment was changed June 1 to a cell proliferation matrix consisting of an aqueous gel containing 1.0 percent by weight of a sodium hyarulonate. In other respects the peroral treatment with Solvezink, Vitamineral, Apresolin Albyl Minor and Persantin was unchanged. During the earlier treatment for 3 months the size of the ulcus is reduced approximately 50% from 1.80 $cm^2$ (Mar. 2, 1990) to 0.96 $cm^2$ (May 30, 1990). Following hyaluronic acid treatment the ulcus-area was reduced by 90% from 0.96 $cm^2$ to 0.08 $cm^2$ (Sep. 5, 1990). The metabolic control was unchanged during the period of observation.

CASE 2)

The following outlines the treatment of a male patient, 67 years of age, with Diabetes Mellitus of type 1 known since 1940, which has been insulin-treated. The Patient suffers with complications in the form of retinopathy, cataract, neuropathy, macroangiopathy with angina pectoris, and is suspected of having had a heart attack in 1989 and hypertonia since 1964, and also nephropathy with proteinuria and impaired renal function with increased S-creatinine, approximately 140 $\mu$mol/l. In May 1989 the patient's right big toe was amputated after chronic ulcus which was infected. The ulcus after amputation was very slow-healing, and the patient was remitted to the Department of Endocrinology, Karolinska Sjukhuset, Stockholm, Sweden, in September 1989. The slow-healing of the ulcus was partly due to recurrent infections, impaired circulation, loss of peripheral pulses, and neuropathy with nasty edema in the ulcus-area. The patient was treated with antibiotics perorally wand locally by revification with Jodosorb, sodium chloride compresses and fibrinolytic treatment.

The size of the ulcus:

| | | |
|---|---|---|
| September, 1989 | 30 × 20 mm | depth 18 mm |
| January 30, 1990 | 15 × 24 mm | depth 11 mm |
| March 21, 1990 | 16 × 10 mm | depth 5 mm |
| May 30, 1990 | 12 × 7 mm | depth 7 mm |

On May 30 local treatment with a cell proliferation matrix consisting of a 1.0 percent by weight aqueous gel of sodium hyaluronate starts, accelerating the healing and on Aug. 8, 1990, the ulcus is 3×7 mm, depth 3.5 mm. On Oct. 3, 1990, the ulcus has healed, despite impaired circulation, which failed to be treated.

CASE 3)

The following outlines the treatment of a male patient, 43 years of age, with Diabetes Mellitus since 1958 and with multiple complications in the form of grave retinopathy (blind), neuropathy, nephropathy. The patient had his kidney transplanted in 1987 and the left lower part of his leg was amputated in 1975, in connection with a traffic accident. The patient has, has since 1987 a chronic ulcus which has not healed on the right heel. Earlier in the 1980s he has had recurrent ulcera in the same area and gangrenously infected ulcus on the same foot second toe, which has caused several periods of treatment in the Department of Endocrinology at Karolinska Sjukhuset and in the diabetes infection clinic. The patient has also had recurrent problems with ulcus and osteitis in the left amputated stump, which has also led to hospitalization and intensified therapy with antibiotics.

Since the kidney transplantation in 1987 the patient has been treated with Prednisolon, 10 mg daily, Imurel 50 mg daily, Sandimmun 250 mg daily and Azatioprin 10 mg daily. Due to recurrent infection with septic influence the patient has been treated from March 26 to July 2 in the Department of Endocrinology at Karolinska Sjukhuset. Before that the patient has been treated in the diabetes infection clinic at the beginning of Mar. 1989 under the same diagnosis.

Despite intensified treatment with antibiotics, local treatment and unloading, previously with patellar tendon bearing-ortosis and finally attempts with a plaster treatment, the heel ulcus did not heal, which was assessed to partly be due to a chronic osteomyelitis. A treatment with Gentamycin locally for several months gave effect on infection parameters in the blood with normalization of reactive protein, improvement of the blood status (Hb, LPK). The patient was sent home from hospital for a stay in the countryside on Jul. 3, 1990, and at the same time the treatment with a cell proliferation matrix consisting of a 1.0 percent by weight aqueous sodium hyaluronate gel was started locally for installation directly into the ulcus cavity.

The size of the ulcus was prior to the treatment approximately 30×25×27 mm with an ulcus depth of 50 mm. On Aug. 15, 1990, it was observed that the ulcus had healed with the exception of a little retained fistula hole which was 4×4 mm with a retained fistel of 50 mm. On September 5 further shrinking of the fistula passway was observed, despite raising signs of local osteomyelitis in the metatarsal bone.

Throughout the period of observation the patient has been treated with antibiotics; Flagyl and Cloxacillin or Ciproxin.

I claim:

1. A method of treating Ulcus Varicosum Cruris or ulcera caused by Diabetes Mellitus, which comprises topically administering to a patient in need of such treatment a therapeutically effective amount of a cell proliferation matrix consisting essentially of an aqueous gel of dissolved hyaluronic acid or a pharmaceutically acceptable salt thereof, wherein the hyaluronic acid or its salt is obtained from Streptococcus and is free of animal DNA or RNA.

2. The method according to claim 1 wherein the aqueous gel comprises 98.0 to 99.9% by weight of water or phosphate buffered saline solution and 0.1 to 2.0% by weight of sodium hyaluronate.

3. The method according to claim 2 wherein the sodium hyaluronate has an average molecular weight of at least 25,000 Da.

4. The method according to claim 3 wherein said sodium hyaluronate has an average molecular weight of $1.2 \times 10^6$ to $2.5 \times 10^6$ Da.

5. The method according to claim 4, wherein said aqueous gel contains 1.0% by weight of sodium hyaluronate having an average molecular weight of $1.2 \times 10^6$ Da.

6. The method according to claim 5 wherein the aqueous gel comprises 98.0 to 99.9% by weight of water or phosphate buffered saline solution and 0.1 to 2.0% by weight of sodium hyaluronate having an average molecular weight of $1.2 \times 10^6$ to $2.5 \times 10^6$ Da.

7. The method according to claim 1 wherein the hyaluronic acid or pharmaceutically acceptable salt thereof is obtained from *Streptococcus equi*.

8. The method according to claim 7 wherein the aqueous gel comprises 98.0 to 99.9% by weight of water or phosphate buffered saline solution and 0.1 to 2.0% by weight of sodium hyaluronate.

9. The method according to claim 8 wherein the sodium hyaluronate has an average molecular weight of at least 25,000 Da.

10. The method according to claim 9 wherein said sodium hyaluronate has an average molecular weight of $1.2 \times 10^6$ to $2.5 \times 10^6$ Da.

11. The method according to claim 10, wherein said aqueous gel contains 1.0% by weight of sodium hyaluronate having an average molecular weight of $1.2 \times 10^6$ Da.

12. The method according to claim 1 wherein the aqueous gel comprises 98.0 to 99.9% by weight of water or phosphate buffered saline solution and 0.1 to 2.0% by weight of sodium hyaluronate having an average molecular weight of $1.2 \times 10^6$ to $2.5 \times 10^6$ Da.

* * * * *